US010895616B2

(12) United States Patent
Duensing et al.

(10) Patent No.: US 10,895,616 B2
(45) Date of Patent: Jan. 19, 2021

(54) APPARATUS FOR HANDLING OPTICAL FIBER IN MAGNETIC RESONANCE IMAGING SYSTEM

(71) Applicant: KONINKLIJKE PHILIPS N.V., Eindhoven (NL)

(72) Inventors: George Randall Duensing, Gainsville, FL (US); Olli Tapio Friman, Gainsville, FL (US)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 16/085,626

(22) PCT Filed: Mar. 22, 2017

(86) PCT No.: PCT/EP2017/056805
§ 371 (c)(1),
(2) Date: Sep. 17, 2018

(87) PCT Pub. No.: WO2017/162729
PCT Pub. Date: Sep. 28, 2017

(65) Prior Publication Data
US 2019/0094317 A1    Mar. 28, 2019

Related U.S. Application Data

(60) Provisional application No. 62/311,452, filed on Mar. 22, 2016.

(51) Int. Cl.
*G01R 33/36*    (2006.01)
*G01R 33/28*    (2006.01)
*A61B 5/055*    (2006.01)
*G01R 33/3415*    (2006.01)

(52) U.S. Cl.
CPC .......... *G01R 33/3692* (2013.01); *A61B 5/055* (2013.01); *G01R 33/28* (2013.01); *G01R 33/3415* (2013.01); *G01R 33/3621* (2013.01)

(58) Field of Classification Search
CPC .... A61B 5/055; G01R 33/28; G01R 33/3415; G01R 33/3621; G01R 33/3692
USPC .................................................. 324/318, 307
See application file for complete search history.

(56) References Cited

U.S. PATENT DOCUMENTS

| 3,378,736 | A | * | 4/1968 | Vale ...................... H01M 10/46 429/7 |
| 5,953,207 | A | * | 9/1999 | Aakalu .............. H05K 7/20163 165/185 |
| 7,173,426 | B1 |   | 2/2007 | Bulumulla et al. |
| 7,378,844 | B2 |   | 5/2008 | Watkins et al. |
| 8,295,905 | B2 | * | 10/2012 | Graves ................... G01R 33/28 600/411 |
| 8,324,899 | B2 |   | 12/2012 | Hoogeveen |

(Continued)

FOREIGN PATENT DOCUMENTS

| DE | 102008035617 A1 | 2/2010 |
| KR | 2011137510 A | 12/2011 |
| WO | 2009144639 A2 | 12/2009 |

*Primary Examiner* — Steven L Yeninas

(57) ABSTRACT

An apparatus includes a takeup spool disposed at a far end of a magnetic resonance imaging bore. The takeup spool is adapted to release optical fiber, and to retract the optical fiber. The apparatus also comprises a dongle configured to connect to a terminal end of the optical fiber.

29 Claims, 6 Drawing Sheets

(56) References Cited

U.S. PATENT DOCUMENTS

| | | | |
|---|---|---|---|
| 8,467,847 B2* | 6/2013 | Caruba | A61B 6/56 600/411 |
| 8,909,320 B2* | 12/2014 | Jenkins | G01R 33/28 600/411 |
| 9,439,735 B2* | 9/2016 | Guttman | A61B 34/20 |
| 9,845,124 B1* | 12/2017 | Ingram | B60L 8/003 |
| 2005/0202310 A1* | 9/2005 | Yahnker | B25F 5/008 429/62 |
| 2007/0036506 A1 | 2/2007 | Kewitsch | |
| 2007/0164746 A1 | 7/2007 | Jevtic et al. | |
| 2008/0118207 A1* | 5/2008 | Yamamoto | G02B 6/4457 385/88 |
| 2008/0191695 A1 | 8/2008 | Van Helvoort et al. | |
| 2008/0309341 A1 | 12/2008 | Dooms et al. | |
| 2009/0030305 A1 | 1/2009 | Hoogeveen | |
| 2009/0041413 A1* | 2/2009 | Hurley | G02B 6/4457 385/101 |
| 2009/0057540 A1* | 3/2009 | Nyffenegger | G01D 5/2515 250/227.11 |
| 2010/0191069 A1* | 7/2010 | Fisher | G06F 1/163 600/300 |
| 2013/0176029 A1* | 7/2013 | Oosawa | A61B 5/0555 324/321 |
| 2014/0361769 A1* | 12/2014 | Hardie | G01R 33/34 324/307 |
| 2015/0131959 A1* | 5/2015 | Zhuang | G02B 6/4457 385/135 |
| 2016/0061916 A1 | 3/2016 | Duensing et al. | |
| 2016/0228005 A1* | 8/2016 | Bammer | A61B 3/112 |
| 2016/0322155 A1* | 11/2016 | Bailey | G01R 33/28 |
| 2017/0045703 A1* | 2/2017 | Pitwon | G02B 6/4457 |
| 2017/0105313 A1* | 4/2017 | Shedd | H05K 7/20309 |
| 2017/0336484 A1* | 11/2017 | Fuderer | G01R 33/36 |
| 2018/0128888 A1* | 5/2018 | Ropella | G01R 33/283 |
| 2019/0055105 A1* | 2/2019 | Benson | B64F 3/02 |
| 2019/0383890 A1* | 12/2019 | Olesen | G01R 33/36 |

* cited by examiner

APPARATUS FOR HANDLING OPTICAL FIBER IN MAGNETIC RESONANCE IMAGING SYSTEM

CROSS REFERENCE TO RELATED APPLICATIONS

This application is a U.S. national phase application of International Application No. PCT/EP2017/056805, filed on Mar. 22, 2017, which claims the benefit of U.S. provisional Application Ser. No. 62/311,452 filed on Mar. 22, 2016 and is incorporated herein by reference.

BACKGROUND

Magnetic resonance imaging (MRI) systems often use body coils disposed over a patient examination space of an MR imaging system for imaging a whole body to be examined, and RF/MR surface or local coils which are directly arranged on a local zone or area to be examined.

Radio frequency (RF) coils acquire analogue signals that are sampled and digitized. In some modern coils, the digitization happens locally, for example within the coil housing.

In known systems, electrical (DC) power, and often signals are provided to and from the local coil by an electrical cable that is connected to the system. The cable often also includes a signal transmission line, such as a coaxial cable for transmission of data from the local coil. These cables are cumbersome, requiring significant shielding when inserted into the bore of the MRI device. Moreover, the RF cables can become excessively hot and cause burns.

What is needed, therefore, is an apparatus that overcomes at least the shortcomings described above.

SUMMARY

In accordance with a representative embodiment, an apparatus comprises a takeup spool disposed at a far end of a magnetic resonance imaging bore. The takeup spool is adapted to release optical fiber, and to retract the optical fiber. The apparatus also comprises a dongle configured to connect to a terminal end of the optical fiber.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
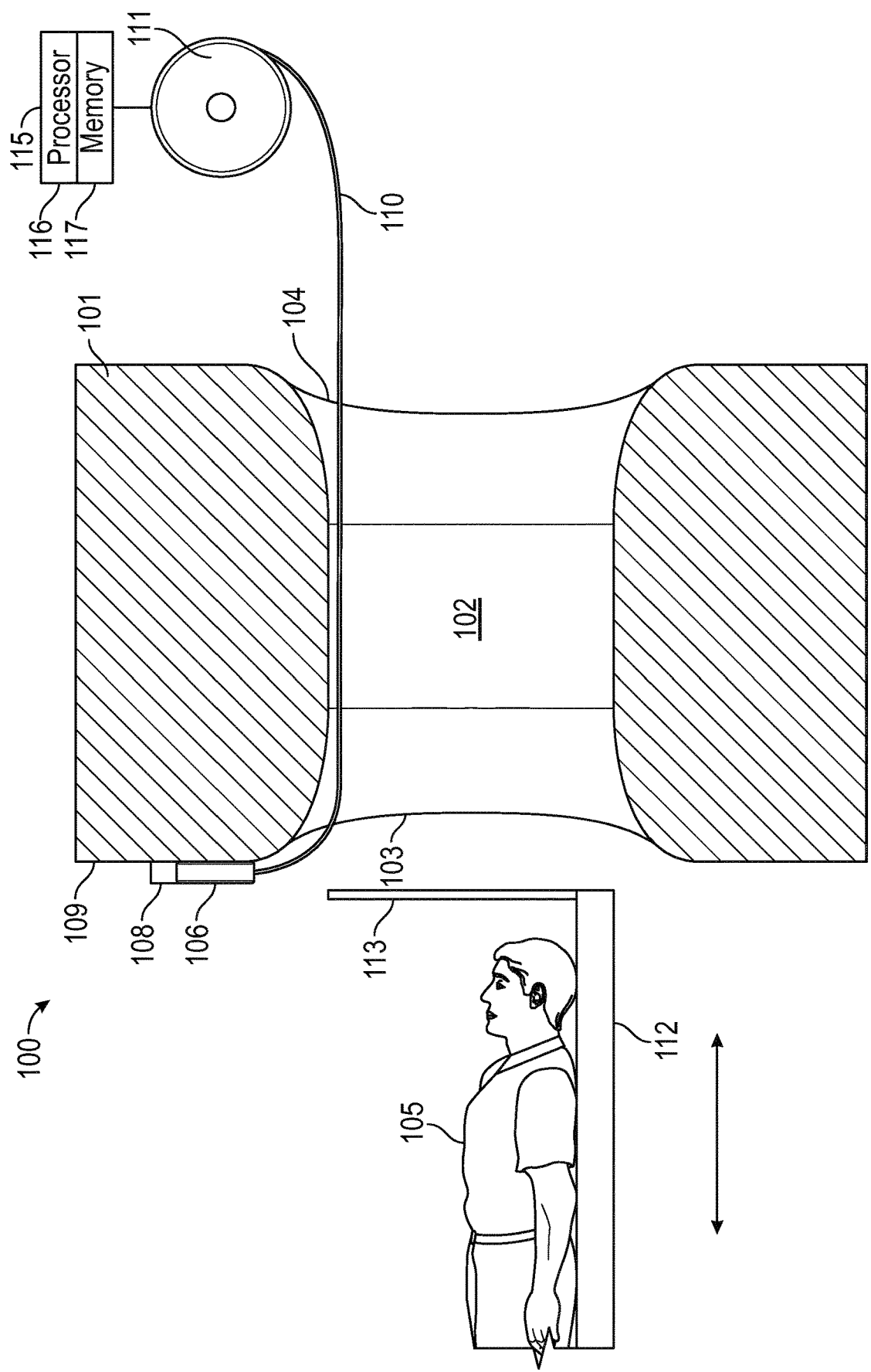
FIG. 1 is a side view of an MRI system in accordance with a representative embodiment.

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms 'a', 'an' and 'the' comprises both singular and plural referents, unless the context clearly dictates otherwise. Thus, for example, 'a device' includes one device and plural devices.

As used herein, the statement that two or more parts or components are "connected" shall mean that the parts are joined or operate together either directly or indirectly, i.e., through one or more intermediate parts or components, so long as a link occurs.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

FIG. 1 is a side view of an MRI system 100 in accordance with a representative embodiment. The MRI system 100 comprises a magnetic structure 101 with a bore 102 extending therethrough for receiving a patient 105. The bore 102 has a near end 103 and a far end 104. Other components of the MR structure, including various electrical and electronic components within the purview of one of ordinary skill in the art are contemplated by the present teachings, but are often not described to avoid obscuring the present teachings.

A dongle 106 is shown connected to an apparatus 108, which is attached to an outer surface 109 of the magnet structure 101. As described more fully below, when the dongle is connected to the apparatus, a spent battery (not shown in FIG. 1A), or a spent heat sink (not shown in FIG. 1A) can be exchanged with a fresh battery, and heat sink, respectively.

An optical fiber 110 is connected to the dongle 106 at one end, extends through the bore 102, and is disposed around a takeup spool 111. As described more fully below, the takeup spool 111 releases the optical fiber 110, to extend a needed length to the dongle 106, and retracts as the dongle 106, which moves with the patient 105, and is extended into the bore 102. Notably, the takeup spool 111 maintains substantially constant tension on the optical fiber 110 in order to avoid tangling of the optical fiber 110 with components of the MRI system 100. Finally, and as described more fully below, when the dongle 106 is outside the near end 103 (e.g., when the dongle 106 is disposed on the patient as described below), the optical fiber is extended to a maximum length. By contrast, when the patient enters the bore 102 to the greatest extent toward the far end 104, the optical fiber 110 is retracted by the takeup spool 111, and is extended to a minimum length.

The MRI system 100 also comprises a table 112 on which the patient 105 rests. An optical fiber guide 113 is attached to the table 112 and maintains the optical fiber 110 at a desired height above the table 112. The table 112 is adapted to move into and out of the bore as indicated by the arrows. As described more fully below, in accordance with a representative embodiment, the table 112 moves in coordination with the takeup spool 111 to maintain a desired degree of tension in the optical fiber 110.

The MRI system 100 also comprises a controller 115, comprising a processor 116 and a memory 117. As described more fully below, the controller 115 is generally configured to provide one or more control commands to coordinate movement (i.e., release and retraction) of the optical fiber 110 from the takeup spool 111 in coordination with the table 112, so that the optical fiber is maintained at a sufficient tension to prevent its descending too much toward the patient, but not too taught that breakage of the optical fiber 110 could occur. This coordination ensures that the proper tension is applied to the optical fiber, especially during its release and retraction from the takeup spool.

Figure 2:
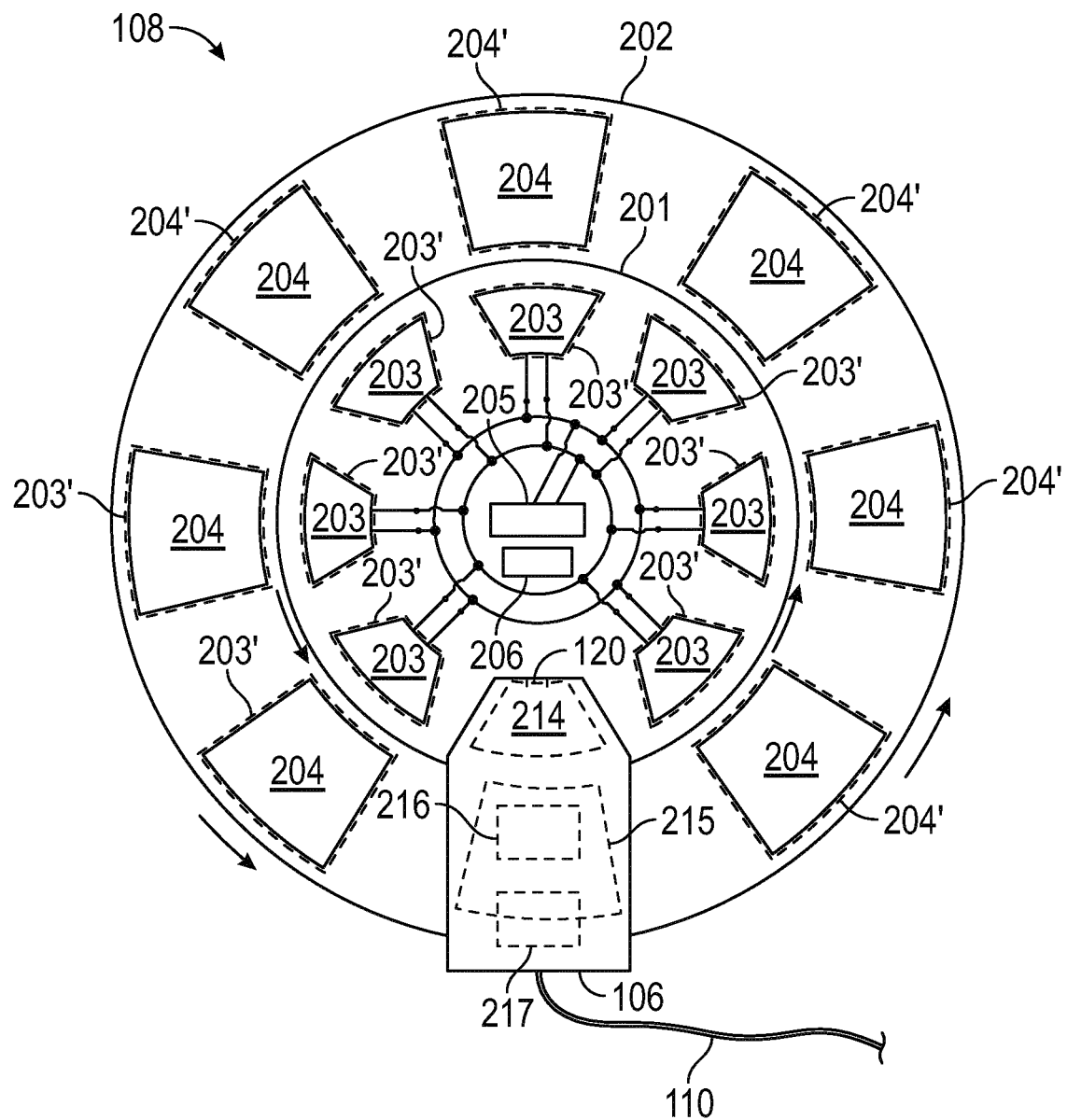
FIG. 2 is a front view of an apparatus in accordance with a representative embodiment.

FIG. 2 is a front view of apparatus 108 in accordance with a representative embodiment. Often, various aspects and details of the various elements described above in connection with the representative embodiments described in connection with FIG. 1 are common to those of the representative embodiments described in connection with FIG. 2. These common aspects and details may not be repeated in order to avoid obscuring the description of the presently described representative embodiments.

The dongle 106 is inserted into the apparatus 108. The dongle 106 comprises a DC power source, which is illustratively a battery 214. As described more fully below, the battery 214 is adapted to be removed and replaced with a more fully charged battery. Moreover, and as described more fully below, the dongle 106 illustratively comprises a transceiver 216 configured to receive and transmit data received during a scan, as well as to transmit and receive other signals as needed. The dongle 106 may also comprise a heat sink (not shown in FIG. 1A), which like the battery is adapted to be removed and replaced with another heat sink. Finally, the dongle 106 may also comprise a memory 217 that stores data received by the transceiver during a scan.

The optical fiber 110 is optionally connected to the dongle 106. The optical fiber 110 is adapted to receive data from the local coil (not shown in FIG. 2) received during the scan and transmit the data to a computer (not shown), which provides MR images to a clinician based on the data. Notably, the optical fiber 110 can be used in addition to other data transmission methods (e.g., the transceiver in the dongle 106) to provide redundancy.

The apparatus 108 comprises a first carousel 201 and, optionally, a second carousel 202.

The first carousel 201 comprises a plurality of charge sites 203' into which a plurality of batteries 203 are disposed, with one battery 203 being disposed in a respective one of the charge sites 203'.

The second carousel 202 comprises a plurality of heat sink sites 204' into which a plurality of heat sinks 204 are disposed, with one heat sink 204 being disposed in a respective one of the heat sink sites 204'.

The apparatus 108 also comprises a battery charger 205. As depicted, the battery charger 205 is selectively connected to each of the charge sites 203', and is configured to charge the batteries 203 as described more fully below.

The apparatus 108 optionally comprises a monitor 206. The monitor 206 is configured to receive charge state information from the battery charger 205 or from each of the batteries 203 directly. As described more fully herein, charge state information can be used to select one of the plurality of batteries 203 that has the greatest charge, so that battery can be provided to the dongle 106.

As depicted by arrows in FIG. 2, the first and second carousels 201, 202 are configured to move together or independently. Generally, the first and second carousels 201, 202 are configured to increment by one position of a battery 203, and a heat sink 204, respectively, by action of an actuator (not shown), which is illustratively a stepper motor or similar device allowing for comparatively precise motion and stopping. The movement of the first carousel 201 increments a battery 203 into position for receipt by the dongle 106, while moving battery 214 out of the dongle 106 and into a vacant charge site 203'. As such, there is always one empty charge site 203' for receipt of the battery 214 from the dongle 106.

In simplest operation, when the dongle 106 is inserted into the apparatus 108 such as depicted in FIG. 1, the battery 214 is disposed in the vacant charge site 203', the first carousel 201 advances so a charged battery 203 is aligned with the dongle 106, and the charged battery 203 is inserted into the dongle 106. Removal of the dongle 106 thus leaves an empty charge site 203'.

Similarly, the movement of the second carousel 202 increments a heat sink 204 into position for receipt by the dongle 106, while moving heat sink 215 out of the dongle 106 and into a vacant heat sink site 204'. As such, there is always one empty heat sink site 204' for receipt of the heat sink 215 from the dongle 106.

When the dongle 106 is inserted into the apparatus 108, the heat sink 215 is disposed in the vacant heat sink site 204', the second carousel 202 advances so a heat sink 204 is aligned with the dongle 106, and the heat sink 204 is inserted into the dongle 106. Removal of the dongle 106 thus leaves an empty heat sink site 204'.

Figure 3A:
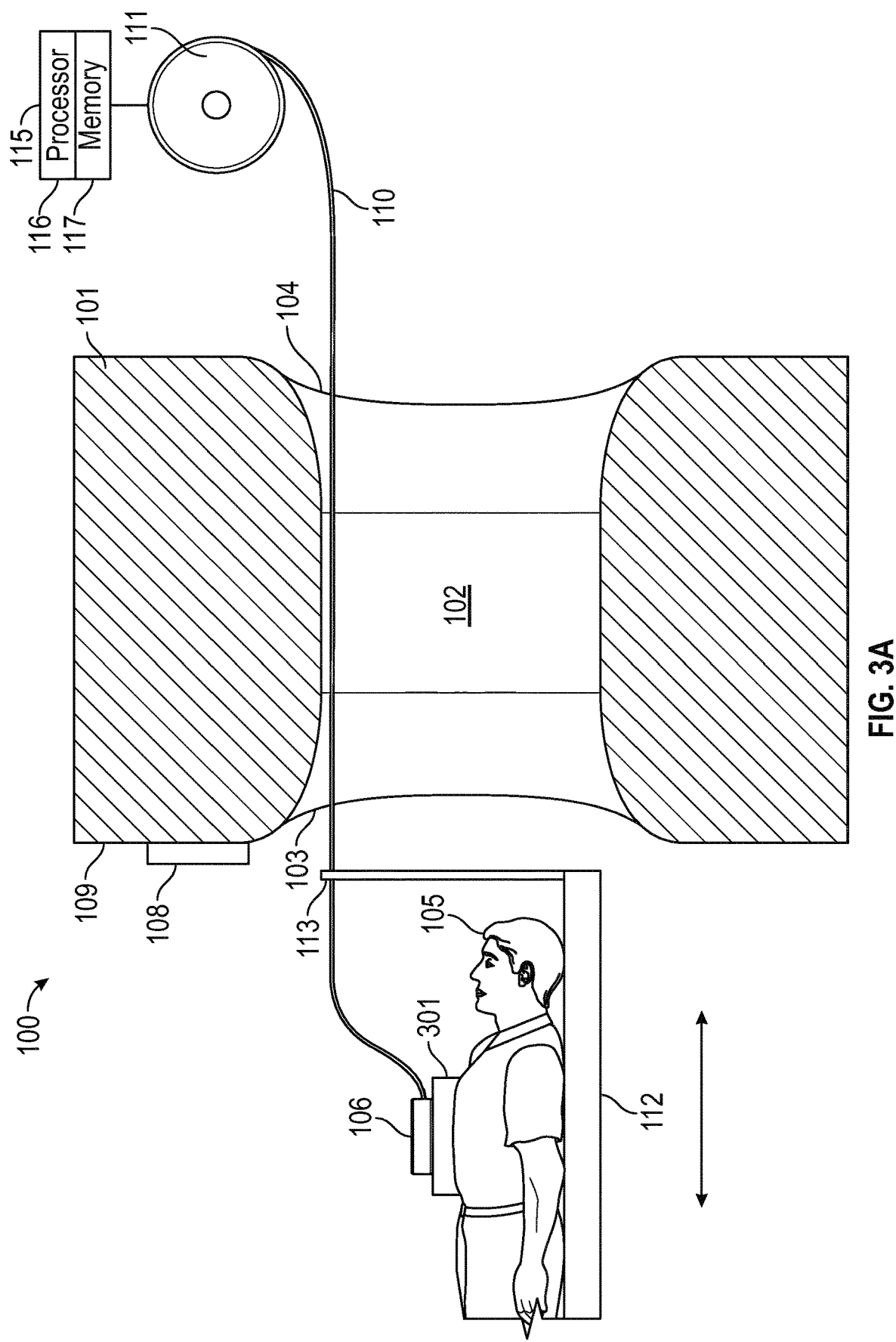
FIG. 3A is a side view of an MRI system in accordance with a representative embodiment.
Figure 3B:
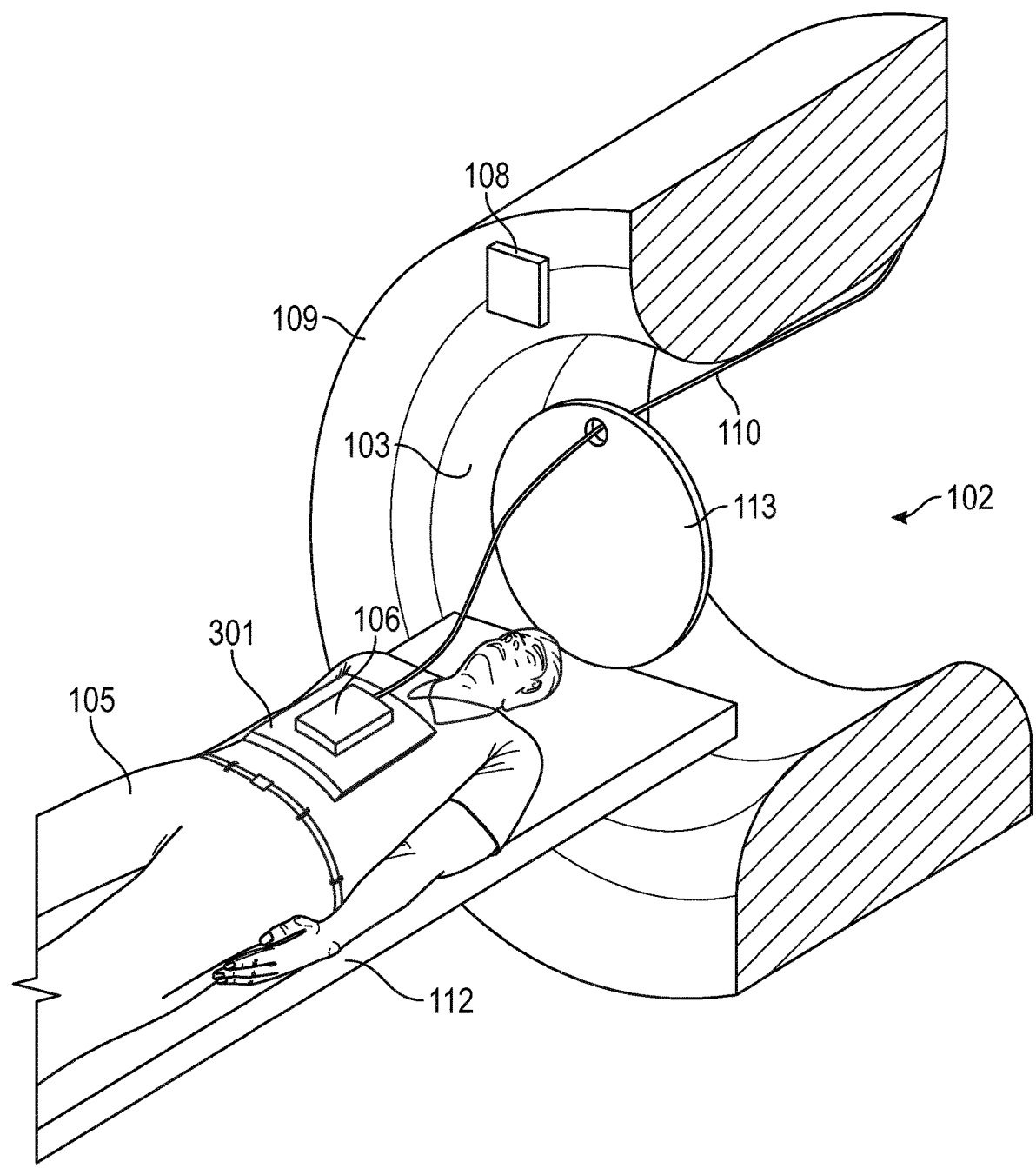
FIG. 3B is a perspective view of the MRI system shown in FIG. 3A.

FIGS. 3A and 3B are side and perspective views, respectively, of MRI system 100 in accordance with a representative embodiment. Again, various aspects and details of the various elements described above in connection with the representative embodiments described in connection with FIGS. 1-2 are common to those of the representative embodiments described in connection with FIG. 3. These common aspects and details may not be repeated in order to avoid obscuring the description of the presently described representative embodiments.

As depicted in FIGS. 3A-3B, the dongle 106 has been removed from apparatus 108 and connected to a local coil 301, in a manner described more fully below in connection with FIG. 4.

The optical fiber 110 is attached to the dongle 106, extending through the near opening of the bore 102, through an opening or void formed in a portion of the optical fiber guide 113.

As the table 112, and thus the patient 105, is moved along the movement direction depicted by the arrows, the controller 115 sends commands to an actuator (not shown) that causes the takeup spool 111 to retract the optical fiber 110 and maintain a desired tension on the optical fiber 110. Notably, the actuator could be a known electric motor, such as a servo motor, selected to turn the takeup spool 111 counterclockwise to release more optical fiber 110 (i.e., as the table 112 moves toward the near end 103), and clockwise to retract more optical fiber 110 (i.e., as the table 112 moves toward the far end 104).

A strain gauge (not shown) can be used to provide real-time feedback of the strain on the optical fiber 110 to the controller 115. The controller 115 can then calculate the required force to be applied to the takeup spool 111 to maintain the tension on the optical fiber 110 at a predetermined position at a desired level. Moreover, the controller 115 may also coordinate movement of the table 112 with the rate of release and rate of retraction of the optical fiber 110 to maintain the tension on the optical fiber 110 at all times. To this end, and by way of example, an electric motor (not shown) can be used to move the table 112 into and out of the bore 102 to a desired position, and at a desired rate. Based on calculations made by the processor 116, the controller 115 is configured to send commands to the electric motor associated with the table 112, and to the actuator associated with the takeup spool 111 to move, and to rotate, respectively, in directions and at rates to maintain the tension on the optical fiber 110 at a desired level.

As described above, the processor 116 is configured to acquire and process data based on inputs from the strain gauge and motion detectors associated with the table 112. The memory 117 stores machine readable instructions (programs) configured to be executed by the processor 116. As will be appreciated by one of ordinary skill in the art, the memory 117 is a non-transitory computer-readable medium having stored therein these machine readable instructions configured to be executed by a processor 116 to perform various methods, such as controlling the release and retraction of the optical fiber 110 on the takeup spool 111, in coordination with the movement of the table 112.

The processor 116 may comprise one or more microprocessors that may be programmed using software (e.g., microcode) to perform various functions discussed herein. Notably, the processor 116 may comprise more than one processor or processing core. The processor 116 may for instance be a multi-core processor. The processor 116 may also comprise a collection of processors within a single computer system (not shown) or distributed among multiple computer systems (not shown) associated with the MRI system 100. As will be appreciated as the present description continues, many programs have their machine-readable instructions performed by the processor 116 that may be within the same computing device or which may even be distributed across multiple computing devices.

Examples of components that may be employed as the processor 116 in various embodiments of the present disclosure include, but are not limited to, conventional microprocessors, microcontrol units, application specific integrated circuits (ASICs), and field-programmable gate arrays (FPGAs).

The memory 117 is configured to store software useful to the processor 116, and may be configured to store various types of data gathered during the movement of the patient 105 during a scan.

Furthermore, the memory 117 stores machine readable instructions configured to be executed by the processor 116 to control the takeup spool 111, and optionally, the table 112. These instructions (programs) are encoded in the memory 117, and when executed on the processor 116, perform at least some of the functions discussed herein. (The terms "program" or "computer program" are used herein in a generic sense to refer to any type of computer code (e.g., software or microcode) that can be employed to program the processor 116.) For example, and as described above, and below, machine readable instructions stored in memory 117 are configured to be executed by the processor 116 to control the takeup spool 111 and table 112 during a scan to ensure the optical fiber 110 is maintained at a sufficient tension to ensure that it does not sag or otherwise interfere with the motion of the patient 105 during a scan.

The memory 117 may comprise non-volatile computer memory, or volatile computer memory, or both, including, but not limited to: a floppy disk, a magnetic hard disk drive, a solid state hard disk, flash memory, a USB thumb drive, Random Access Memory (RAM), Read Only Memory (ROM), programmable read-only memory (PROM), electrically programmable read-only memory (EPROM), electrically erasable and programmable read only memory (EEPROM), universal serial bus (USB) drive, floppy disks, compact disks (CDs), optical disks, magnetic tape, a smart card, a digital versatile disc (DVD), a CD-ROM, a solid state hard drive, an optical disk, a magneto-optical disk, and a register file of the processor. Examples of optical disks include Compact Disks (CD) and Digital Versatile Disks (DVD), for example CD-ROM, CD-RW, CD-R, DVD-ROM, DVD-RW, or DVD-R disks. Various storage media may be fixed within the processor 116 or may be transportable, such that the one or more programs stored thereon can be loaded into the processor 116 so as to implement various aspects of the present teachings discussed herein.

Figure 4:
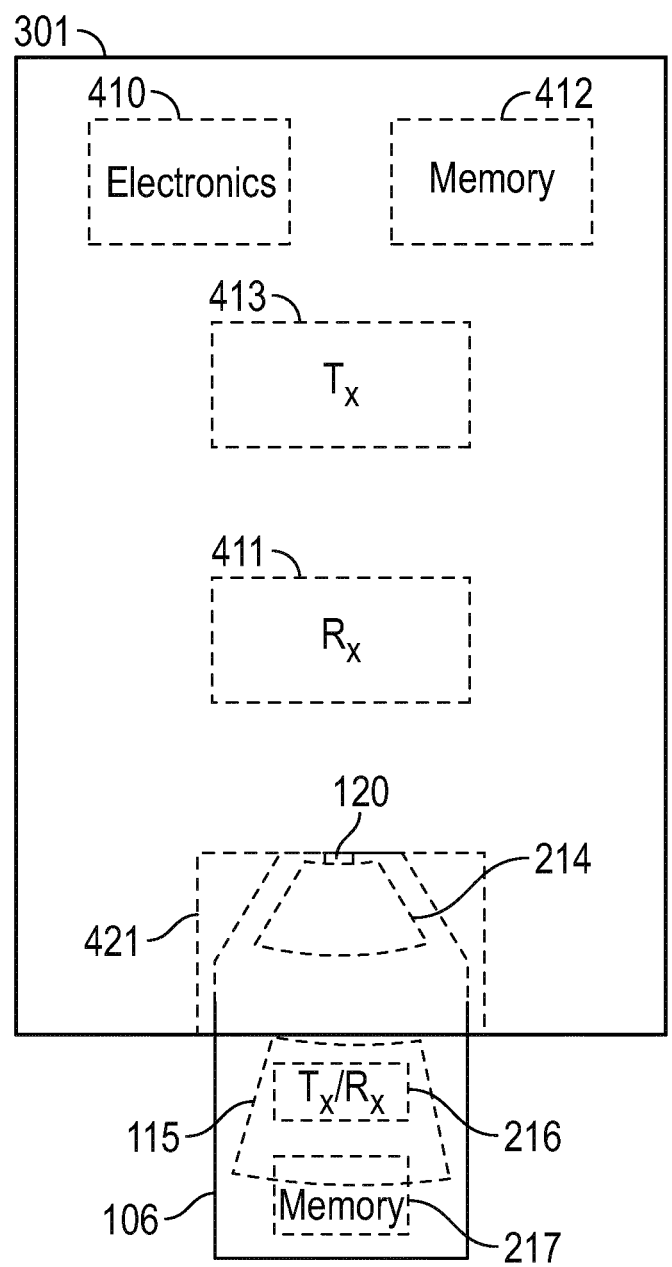
FIG. 4 is a top view of an RF coil with a dongle connected thereto in accordance with a representative embodiment.

FIG. 4 is a top view of the local coil 301 with dongle 106 connected thereto, in accordance with a representative embodiment.

The local coil 301 illustratively comprises electronics 410 configured to receive data from a receiver 411, and to digitize the data from storage in a memory 412. The electronics 410 illustratively comprises electronic and electrical components for digitizing the data for further use in constructing images based on the MR scan of the patient 103.

The analog signals induced in RF coils of the local coil 301 by the nuclear spins are generally amplified with a low noise amplifier and digitized using one or more analog to digital converters (A/D) (not shown) provided, for example, in the local coil 301. By way of example, a bandpass delta sigma A/D may be used in this capacity. Notably, variable gain or compression may be used to cover the entire dynamic range of the possible signals and noise. The digitized data is typically compressed with little or substantially no loss, encoded for error correction, and serialized for transmission.

The local coil 301 also comprises, optionally, a transmitter 413. In certain embodiments, the transmitter 413 is an RF transmitter and usefully transmits the data from the memory 412 to a computer or other device, where the data are used to reconstruct the MR image from the patient scan. Alternatively, and as noted below, the transmission of data may be along an optical waveguide (e.g., optical fiber 110), which is connected to the local coil 301. In this case, the transmitter 413 would comprise an optical transmitter.

The dongle 106 comprises a battery 214, a heat sink 215, and optionally, a transceiver 216, and a memory 217.

The transceiver 216 may comprise a separate transmitter and receiver. Alternatively, the transceiver 216 is replaced with only a receiver. As mentioned above, data acquired during the scan of the patient 105 may be received by the dongle 106, and stored in memory 217. These data may also be transmitted by the transceiver 216 to a computer or other device, and used to reconstruct the MR image from the patient scan. In other embodiments described below, the data in the memory 217 may be downloaded at the apparatus 108 and sent to the computer or other device. In still other embodiments, the memory 217 may be removable from the dongle, and provided for further use.

The memory 217 may comprise non-volatile computer memory, or volatile computer memory, or both, including, but not limited to: a floppy disk, a magnetic hard disk drive, a solid state hard disk, flash memory, a USB thumb drive, Random Access Memory (RAM), Read Only Memory (ROM), programmable read-only memory (PROM), electrically programmable read-only memory (EPROM), electrically erasable and programmable read only memory (EEPROM), universal serial bus (USB) drive, floppy disks, compact disks (CDs), optical disks, magnetic tape, a smart card, a digital versatile disc (DVD), a CD-ROM, a solid state hard drive, an optical disk, a magneto-optical disk, and a register file of the processor. Examples of optical disks include Compact Disks (CD) and Digital Versatile Disks (DVD), for example CD-ROM, CD-RW, CD-R, DVD-ROM, DVD-RW, or DVD-R disks.

As described above, the battery 214 is rechargeable, and provided in a port in the dongle 106 so that upon insertion into the apparatus 108, the battery 214 may be removed, and recharged by the battery charger of the apparatus 108. As will become clearer as the present description continues, in a representative embodiment, the battery 214 is replaced in the dongle 106 by a battery having a charge level that is greater than that of battery 214.

The battery 214 provides the DC power to the local coil 301, and thereby frees the local coil from the constraints of a connection to a power supply. As alluded to above, known local coils that require connections to a power supply through a cable, among other things, are cumbersome, and impede the work of the clinician. By contrast, because the battery is integral to the dongle 106, no such impediments to the clinician exist.

The battery 214 is a rechargeable battery with charge/power requirements dictated by the local coil 301. While known dry-cell rechargeable batteries (e.g., lithium ion batteries) are contemplated, other known rechargeable portable DC power sources are contemplated by the present teachings. These include, but are not limited to, semiliquid lithium ion fuel cells, nickel-metal-hydride (NiMH) fuel cells, potassium ion fuel cells, and hydrogen fuel cells.

The dongle 106 also comprises a heat sink 215. As can be appreciated, during operation, the discharging battery 214 can create heat. Because the battery 214 is in the dongle 106, which in turn, is disposed in the local coil 301, this heat can contact the patient 105, and can be uncomfortable, if not dangerous to the patient. In such instances, it is useful to provide a heat sink which will dissipate the heat from the battery 214. In certain embodiments, the heat sink 215 is a phase-change device. Phase-change devices comprise a phase-change material (PCM) that undergoes a change of phase during heat transfer to the material. These materials, which are sometimes referred to as high-performance heat transfer materials, are commonly used in heat sinks in electronic applications, and are well known to one of ordinary skill in the art. Alternatively, materials with comparatively high thermal coefficients, such as metals, metal alloys and certain ceramic materials, may be used in the heat sink.

Like the battery 214, the heat sink 215 is also provided in a port, and is configured to be removed and stored by the apparatus 108, and replaced with a 'fresh' heat sink.

The dongle 106 is illustratively inserted into a port 421 of the local coil 301. Once inserted, the dongle 106 is electrically connected to Input/output (I/O) circuitry 120 of the dongle 106. The I/O circuitry 120 varies in complexity based on the requirements of the device to which it is connected. For example, if the dongle 106 is not adapted to receive data from the local coil 301, but rather to provide only DC power thereto, the I/O circuitry can include only a simple electrical connection. By contrast, if the dongle 106 is configured to receive data from the local coil 301, the I/O circuitry may be configured to control communication therebetween, and act as an interface including necessary logic to interpret input and output signals or data to/from the electronics 410. The I/O circuitry 120 may also be configured to receive RF data during the scan and provide this to the transceiver 216, and to transmit data therefrom.

Figure 5:
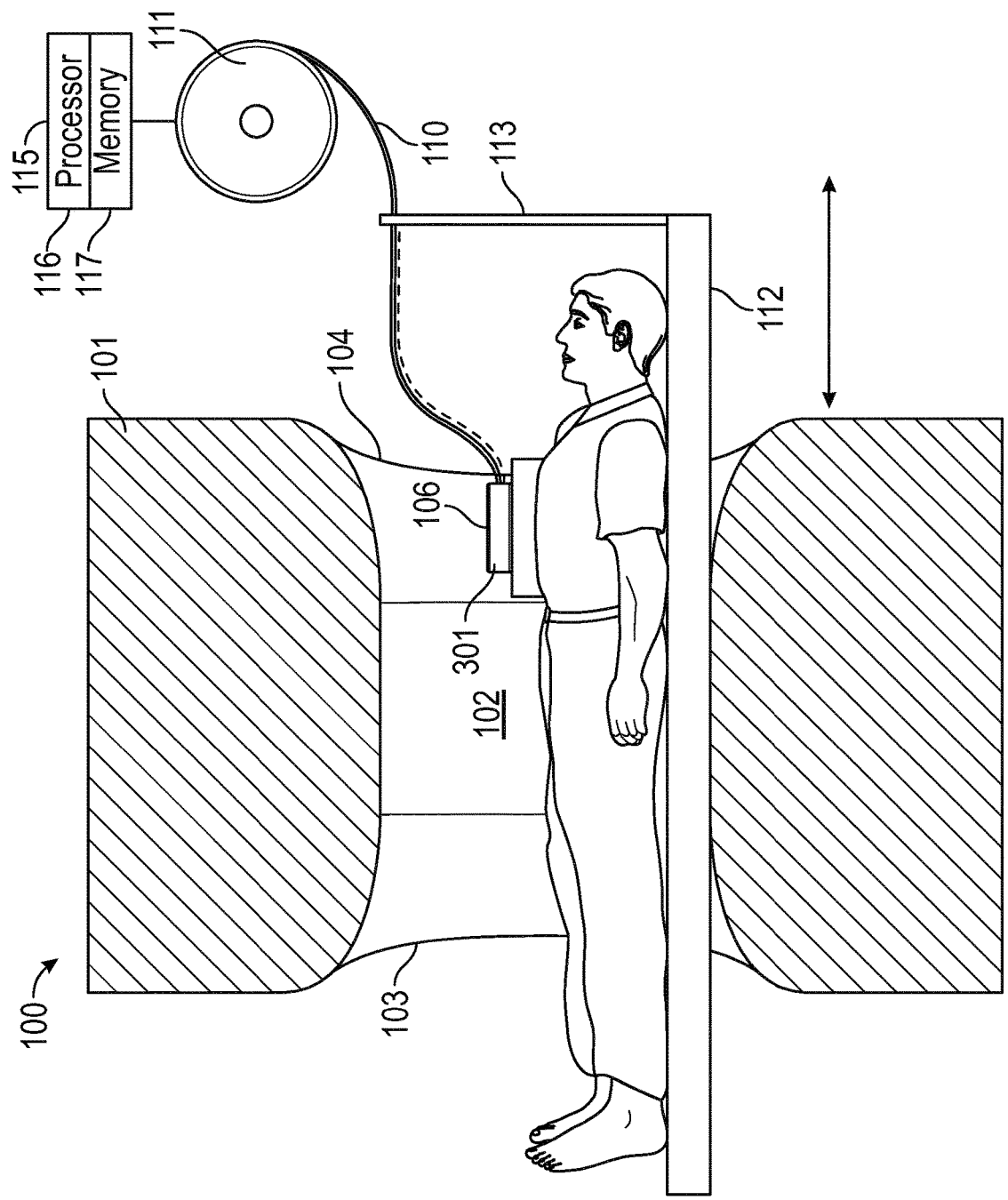
FIG. 5 is a perspective view of an MRI system in accordance with a representative embodiment.

FIG. 5 is a side view of MRI system 100 in accordance with a representative embodiment. Again, various aspects and details of the various elements described above in connection with the representative embodiments described in connection with FIGS. 1-4 are common to those of the representative embodiments described in connection with FIG. 5. These common aspects and details may not be repeated in order to avoid obscuring the description of the presently described representative embodiments.

As depicted in FIG. 5, the table 112 and thus the patient 105, have been moved along the movement direction depicted by the arrows, so the local coil 301 is located at a desired position in the bore 102. As such, compared to the embodiment depicted in FIG. 3, a portion of the optical fiber 110 has been retracted into the takeup spool 111. Notably, as the table is moved through the near end 103 towards the far end 104, and into the bore 102 to the position depicted, the controller 115 sends commands to the actuator (not shown) that causes the takeup spool 111 to retract the optical fiber 110 and maintain a desired tension on the optical fiber 110.

As noted previously, the controller 115 calculates the required force to be applied by the servo or other electric motor to the takeup spool 111 to maintain the tension on the optical fiber 110 at a predetermined position at a desired level. Moreover, the controller 115 may also coordinate movement of the table 112 with the rate of release and rate of retraction of the optical fiber 110 to maintain the tension on the optical fiber 110 at all times. Based on calculations made by the processor 116, the controller 115 is configured to send commands to the electric motor associated with the table 112, and to the actuator associated with the takeup spool 111 to move, and to rotate, respectively, in directions and at rates to maintain the tension on the optical fiber 110 at a desired level.

Finally, when the scan is completed, the table 112 is moved back toward the near end 103 coming to rest in a position such as depicted in FIG. 1. Again, the controller 115 sends commands to the actuator (not shown) that causes the takeup spool 111 to retract the optical fiber 110 and maintain a desired tension on the optical fiber 110, and sends commands to the electric motor associated with the table 112 to move the table 112 at a rate that will maintain the tension on the optical fiber 110.

In view of this disclosure it is noted that the various components can be implemented in a variety of elements and variant structures. Further, the various elements, structures and parameters are included by way of example only and not in any limiting sense. In view of this disclosure, those skilled in the art can implement the present teachings in determining their own applications and needed materials and equipment to implement these applications, while remaining within the scope of the appended claims.

The invention claimed is:

1. An apparatus, comprising:
 a takeup spool disposed at a far end of a magnetic resonance imaging (MRI) bore, the takeup spool adapted to release optical fiber, and to retract the optical fiber;
 an actuator connected to the takeup spool, the actuator adapted to rotate the takeup spool in one direction to retract optical fiber, and in another direction to release the optical fiber;
 a controller configured to provide control commands to coordinate release and retraction of the optical fiber from the takeup spool in coordination with movement of a table into and out of the magnetic resonance imaging bore; and
 a dongle configured to connect to a terminal end of the optical fiber;
 wherein the dongle comprises:
 a battery configured to provide direct current (DC) power to a device to which the dongle is electrically and mechanically connected, the battery being adapted to be removed, and replaced by another battery; and
 a heat sink configured to dissipate heat generated by the battery, the heat sink being adapted to be removed, and replaced by another heat sink.

2. The apparatus as claimed in claim 1, wherein, as the dongle travels into the MRI bore, the takeup spool retracts the optical fiber, and stores the optical fiber in a circular arrangement having a radius great enough to avoid damage to the optical fiber.

3. The apparatus as claimed in claim 2, wherein, when the dongle extends at its greatest distance from a near end of the MRI bore, and into the MRI bore, the optical fiber is retracted to a minimum length.

4. The apparatus as claimed in claim 1, wherein, when the dongle is outside a near end of the MRI bore, the optical fiber is released to a maximum length.

5. The apparatus as claimed in claim 1, wherein the dongle is adapted to connect to a radio frequency (RF) coil disposed over a patient.

6. The apparatus as claimed in claim 5, wherein the dongle comprises a transceiver configured to receive data from the RF coil, and to transmit the data from the dongle through the optical fiber.

7. The apparatus of claim 6, wherein the dongle further comprises a memory device, the memory device being configured to be removed from the dongle, and replaced with another memory device.

8. The apparatus as claimed in claim 1 wherein the actuator comprises a servo motor.

9. The apparatus of claim 1, wherein the coordination of the release and retraction maintains at a sufficient tension to prevent its descending toward the table, but not too taught that breakage of the optical fiber occurs.

10. An apparatus, comprising:
 a takeup spool disposed at a far end of a magnetic resonance imaging (MRI) bore, the takeup spool adapted to release optical fiber, and to retract the optical fiber;
 a dongle configured to connect to a terminal end of the optical fiber, wherein the dongle comprises a transceiver configured to receive data from an RF coil disposed over a patient, and to transmit the data from the dongle through the optical fiber; and
 a controller configured to provide control commands to coordinate release and retraction of the optical fiber from the takeup spool in coordination with movement of a table into and out of the magnetic resonance imaging bore.

11. The apparatus of claim 10, wherein the coordination of the release and retraction maintains at a sufficient tension to prevent its descending toward the table, but not too taught that breakage of the optical fiber occurs.

12. The apparatus as claimed in claim 10, wherein, as the dongle travels into the MRI bore, the takeup spool retracts the optical fiber, and stores the optical fiber in a circular arrangement having a radius great enough to avoid damage to the optical fiber.

13. The apparatus as claimed in claim 12, wherein, when the dongle extends at its greatest distance from a near end of the MRI bore, and into the MRI bore, the optical fiber is retracted to a minimum length.

14. The apparatus as claimed in claim 10, wherein, when the dongle is outside a near end of the MRI bore, the optical fiber is released to a maximum length.

15. The apparatus as claimed in claim 10, wherein the dongle is adapted to connect to a radio frequency (RF) coil disposed over a patient.

16. The apparatus as claimed in claim 15, wherein the dongle comprises a transceiver configured to receive data from the RF coil, and to transmit the data from the dongle through the optical fiber.

17. The apparatus of claim 16, wherein the dongle further comprises a memory device, the memory device being configured to be removed from the dongle, and replaced with another memory device.

18. The apparatus of claim 10, further comprising an actuator connected to the takeup spool, the actuator adapted to rotate the takeup spool in one direction to retract optical fiber, and in another direction to release the optical fiber.

19. The apparatus as claimed in claim 18, wherein the actuator comprises a servo motor.

20. A device for use in a magnetic resonance imaging (MRI) system, comprising:
 a takeup spool disposed at a far end of the MRI bore, the takeup spool adapted to release optical fiber, and to retract the optical fiber; and
 a dongle adapted to be inserted into an apparatus, and configured to connect to a terminal end of the optical fiber;
 wherein the dongle comprises:
 a battery configured to provide direct current (DC) power to a device to which the dongle is electrically and mechanically connected, wherein when the dongle is connected to the apparatus, the battery is adapted to be removed, and replaced by another battery; and a heat sink configured to dissipate heat generated by the battery, wherein when the dongle is connected to the apparatus, the heat sink is adapted to be removed, and replaced by another heat sink.

21. The device as claimed in claim 20, wherein, as the dongle travels into the MRI bore, the takeup spool retracts the optical fiber, and stores the optical fiber in a circular arrangement having a radius great enough to avoid damage to the optical fiber.

22. The device as claimed in claim 21, wherein, when the dongle extends at its greatest distance from a near end of the MRI bore, and into the MRI bore, the optical fiber is retracted to a minimum length.

23. The device as claimed in claim 20, wherein, when the dongle is outside a near end of the MRI bore, the optical fiber is released to a maximum length.

24. The device as claimed in claim 20, wherein the dongle is adapted to connect to a radio frequency (RF) coil disposed over a patient.

25. The device as claimed in claim 24, wherein the dongle comprises a transceiver configured to receive data from the RF coil, and to transmit the data from the dongle through the optical fiber.

26. The device of claim 25, wherein the dongle further comprises a memory device, the memory device being configured to be removed from the dongle, and replaced with another memory device.

27. The device of claim 20, wherein the apparatus comprises a carousel.

28. The device of claim 27, wherein the carousel comprises a charge site into which the battery is disposed when the dongle is connected to the apparatus.

29. The device of claim 28, wherein the carousel is a first carousel, and the apparatus comprises a second carousel comprising a heat sink site into the heat sink is disposed.

* * * * *